United States Patent [19]

Galvan et al.

[11] Patent Number: 5,424,473
[45] Date of Patent: Jun. 13, 1995

[54] PROCESS FOR THE PREPARATION OF ARYL HALOFORMATES AND DIARYL CARBONATES

[75] Inventors: Rafael Galvan; Michael J. Mullins, both of Midland, Mich.

[73] Assignee: The Dow Chemical Company, Midland, Mich.

[21] Appl. No.: 214,863

[22] Filed: Mar. 16, 1994

[51] Int. Cl.⁶ .............................................. C07C 68/02
[52] U.S. Cl. .................................... 558/270; 558/274; 558/260
[58] Field of Search ....................... 558/270, 274, 260

[56] References Cited

U.S. PATENT DOCUMENTS

| | | | |
|---|---|---|---|
| 3,211,774 | 10/1965 | Stephens | 558/281 |
| 3,952,045 | 4/1976 | Gaenzler et al. | |
| 4,102,912 | 7/1978 | Carr | 558/274 |
| 4,217,298 | 8/1980 | Shikata et al. | 558/265 |
| 4,366,102 | 12/1982 | Rauchschwalbe et al. | 558/282 |
| 4,592,872 | 6/1986 | Cagnon et al. | 558/281 |
| 4,592,874 | 6/1986 | Cagnon et al. | 558/283 |
| 4,609,501 | 9/1986 | Mark | 558/270 |
| 5,136,077 | 8/1992 | Rand | 558/274 |

FOREIGN PATENT DOCUMENTS 42-23409 11/1967 Japan.

OTHER PUBLICATIONS

Derwent 88-108804/16, JP-201568 (1986).
Derwent 91-350878/48, JP-029513 (1990).
Chemical Abstracts 66:66016d (1967).
Derwent 92-309731/38, JP-132375 (1991).
Derwent 91-286087/39, JP-329470 (1989).
Derwent 92-401780/49, JP-132376, (1991).
Derwent 91-022179/03, JP-42404 (1990).
Derwent 92-150771/18, JP-257043 (1990).
Derwent 87-350180/50, FR-8537 (1986).

*Primary Examiner*—José G. Dees
*Assistant Examiner*—Dwayne C. Jones
*Attorney, Agent, or Firm*—Marie F. Zuckerman

[57] ABSTRACT

A process of preparing diaryl carbonates, such as diphenyl carbonate, and aryl haloformates, such as phenyl chloroformate. The process involves contacting phenol or a substituted phenol with a carbonyl halide, such as phosgene, in the presence of a phosphorus-containing catalyst. The catalyst is selected from alkyl phosphates, aryl phosphites, aryl phosphates, organic phosphinites and phosphinates, organic pyrophosphates, inorganic phosphorous and phosphoric acids, and phosphorus oxides.

19 Claims, No Drawings

PROCESS FOR THE PREPARATION OF ARYL HALOFORMATES AND DIARYL CARBONATES

BACKGROUND OF THE INVENTION

This invention relates to a process for the preparation of aryl haloformates, such as phenyl chloroformate, and diaryl carbonates, such as diphenyl carbonate, from phenols and carbonyl halides, such as phosgene.

Aryl haloformates and diaryl carbonates are well known as monomers for the production of polycarbonate plastics.

Up to the present time the direct reaction between phenols and phosgene is so slow that the reaction has not been practiced commercially. It is feasible, however, to prepare aryl chloroformates and diaryl carbonates by reacting phenols with phosgene in the presence of a stoichiometric amount of sodium hydroxide. The base reacts with hydrogen chloride liberated in the process to form a stoichiometric amount of waste salt, which disadvantageously must be separated from the product mixture and disposed. More disadvantageously, in commercial applications the process is conducted in a two-phase system comprising water and an organic solvent which reduces the productivity of the process.

It is also known that phenols react with phosgene in the presence of a stoichiometric amount of tertiary amine to yield aryl chloroformates and diaryl carbonates. The tertiary amine reacts with hydrogen chloride liberated in the process to form a stoichiometric amount of amine hydrochloride salt. Disadvantageously, the amine hydrochloride must also be removed from the reaction mixture and disposed. Moreover, the use of tertiary amine requires the process to be conducted in an organic solvent. The waste treatment and use of organic solvent adversely affect the economics of the process.

U.S. Pat. No. 4,366,102 discloses a method of preparing aromatic chloroformic acid esters by reacting phenols and phosgene in a homogeneous liquid phase and in the presence of a catalyst consisting of an organic phosphorus compound. The phosphorus compound is disclosed to be an organic phosphine, phosphine oxide, phosphine halide, phosphonium salt, or halogenophosphine. These compounds are undesirable, because they are expensive. This patent also teaches at Example 3 a comparative experiment wherein phenol and phosgene are heated in the presence of triethyl phosphite to yield predominantly diphenyl carbonate and a minor amount of chloroformic acid phenyl ester.

It would be advantageous to have a process of preparing aryl haloformates and diaryl carbonates which does not require a stoichiometric amount of base, such as, sodium hydroxide or tertiary amine. Such a process would eliminate the need for separating and disposing of or treating a waste salt stream. It would also be desirable if the process did not require expensive catalysts, such as, organic phosphines.

SUMMARY OF THE INVENTION

This invention is a process of preparing an aryl haloformate or a diaryl carbonate. The process comprises contacting a phenol with a carbonyl halide in the presence of a catalytic amount of a phosphorus-containing catalyst. The catalyst is selected from the group consisting of alkyl phosphates, aryl phosphites, aryl phosphates, organic phosphinites and phosphinates, organic pyrophosphates, inorganic phosphorous and phosphoric acids, phosphorus oxides, and combinations thereof. The molar ratio of the carbonyl halide to the phenol is sufficient to produce predominantly an aryl haloformate or a diaryl carbonate product. The contacting of the phenol with the carbonyl halide is conducted under reaction conditions such that an aryl haloformate or a diaryl carbonate is predominantly formed.

Advantageously, the process of this invention produces an aryl haloformate or a diaryl carbonate in good yield and at a commercially acceptable rate of formation. More advantageously, the process of this invention does not require expensive catalysts or stoichiometric amounts of additives. Most advantageously, the process of this invention eliminates the formation of a waste salt stream which must be disposed. Moreover, no amine hydrochloride salts are produced which would have to be removed from the product stream and further treated.

DETAILED DESCRIPTION OF THE INVENTION

The process of this invention involves contacting phenol or substituted phenol with a carbonyl halide in the presence of a phosphorus-containing catalyst to yield predominantly an aryl haloformate or a diaryl carbonate product. The phosphorus-containing catalyst is selected from the group consisting of alkyl phosphates, aryl phosphites, aryl phosphates, organic phosphinites and phosphinates, organic pyrophosphates, inorganic phosphorous and phosphoric acids, phosphorus oxides, and combinations of the aforementioned compounds. In a preferred embodiment of the invention the process involves contacting phenol with phosgene in the presence of at least one of the aforementioned catalysts to prepare phenyl chloroformate or diphenyl carbonate.

The overall reaction which occurs during the process of this invention may be illustrated by the preferred reaction of phosgene with phenol wherein the phosgene/phenol molar ratio is 1/1 to form phenyl chloroformate:

$$C_6H_5OH + COCl_2 \rightarrow C_6H_5O-C(O)-Cl + HCl$$

or by the preferred reaction of phosgene with phenol wherein the phosgene/phenol molar ratio is ½, to form diphenyl carbonate:

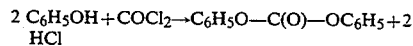

$$2\ C_6H_5OH + COCl_2 \rightarrow C_6H_5O-C(O)-OC_6H_5 + 2\ HCl$$

One or two equivalents of hydrogen chloride are liberated in the process.

Phenol and any substituted phenol are suitable for the process of this invention provided that the phenol is capable of reacting with a carbonyl halide to yield an aryl haloformate or a diaryl carbonate product. As one skilled in the art will recognize, phenol comprises a phenyl ring substituted with one hydroxyl moiety. Substituted phenols comprise the phenyl ring and one hydroxyl moiety, but the phenyl ring is further substituted with one or more hydroxyl moieties or with one or more inert substituents. The term "inert" is taken to mean that the substituent does not inhibit or interfere with the process of this invention. Suitable inert substituents include $C_{1-10}$ aliphatic moieties, as well as, halo, phenyl, and $C_{1-10}$ alkyl-substituted phenyl moieties.

Ether (—OR), keto (—C(O)R) and ester (—COOR) substituents, wherein R is preferably selected from $C_{1-10}$ alkyl, phenyl, and $C_{1-10}$ alkyl-substituted phenyl functionalities are also suitable. Compounds wherein the phenyl ring is fused to a second saturated or unsaturated ring are also acceptable, provided that the phenyl ring is substituted with one or more hydroxyl moieties and is capable of reacting with a carbonyl halide to form an aryl haloformate or diaryl carbonate product. Accordingly, hydroxy-substituted naphthalenes and hydroxy-substituted furans are suitable for the process of the invention.

Non-limiting examples of phenols which can be employed according to the invention include: phenol, o-cresol, m-cresol, p-cresol, 3-(2-pentyl)phenol, 3-(3-pentyl)phenol, xylenols including 3,4-dimethylphenol and 3,5-dimethylphenol, 3,4,5-trimethylphenol, 2-isopropylphenol, 3-isopropylphenol, 3,5-diisopropylphenol, 3-methyl-5-isopropylphenol, 2-isopropoxyphenol, 2-sec-butylphenol, 3-sec-butylphenol, 3-tert-butylphenol, 3,5-di-tert-butylphenol, 2-chlorophenol, 4-chlorophenol, 3,4-dimethyl-6-chlorophenol, hydroquinone, resorcinol, 2-methoxyphenol, 3-methoxyphenol, and 4-methoxyphenol, methyl 4-hydroxyphenyl ketone, phenyl 4-hydroxyphenyl ketone, bis(4-hydroxyphenyl) ketone, 4-hydroxyphenyl acetate, 1-naphthol, 2-naphthol, 5,6,7,8-tetrahydro-1-naphthol, 1,5-dihydroxynaphthalene, 1,1-bis(4-hydroxyphenyl)methane, 1,1-bis-(4-hydroxyphenyl)ethane, 2,2-bis-(4-hydroxyphenyl)propane, 4,4'-cyclohexylidenebisphenol, 4,4'-bishydroxydiphenyl ether, dihydroxybenzophenone, and bis(4-hydroxyphenyl)sulfone. Preferably, the phenol is unsubstituted phenol, cresol, hydroquinone or resorcinol. More preferably, the phenol is unsubstituted phenol or cresol. Most preferably, the phenol is unsubstituted phenol.

A carbonyl halide is required for the process of this invention. Suitable carbonyl halides are represented by the formula $COX_2$ wherein X is chlorine, bromine or fluorine. Other suitable carbonyl halides include "diphosgene" represented by the formula $Cl_3C$—O—C(O)—Cl, as well as bis(trichloromethyl) carbonate, known as "triphosgene" and represented by the formula $Cl_3C$—O—C(O)—O—$CCl_3$. Carbonyl chloride ($COCl_2$), well-known as "phosgene," is the preferred carbonyl halide. Phosgene is typically introduced into the reactor as essentially pure phosgene gas, although it is noted that in commercial samples of phosgene small amounts of carbon monoxide are typically present.

The relative amounts of carbonyl halide and phenol or substituted phenol can vary within any operable range provided that the predominant product is an aryl haloformate or a diaryl carbonate. Typically, if the desired end-product is the aryl haloformate, the carbonyl halide/phenol molar ratio should be greater than 0.5. Preferably, the carbonyl halide/phenol molar ratio ranges between about 0.6 and about 1.2, more preferably, between about 0.6 and about 1.0. Below the typical range of about 0.6, the selectivity to aryl haloformate decreases and a higher amount of diaryl carbonate is formed. There is no particular advantage to using a carbonyl halide/phenol molar ratio above the typical upper limit of about 1.2, because above this ratio a large amount of unreacted carbonyl halide will have to be recovered and recycled. If the desired end-product is diaryl carbonate, the carbonyl halide/phenol molar ratio should be no greater than 0.5. Preferred carbonyl halide/phenol molar ratios range between about 0.1 and 0.5, more preferably, between about 0.25 and about 0.40. Below the lower typical range of 0.1, the conversion of phenol may be low, and the amount of phenol recycle may be high. Above the upper range of 0.5, the selectivity to diaryl carbonate decreases while the selectivity to aryl haloformate increases.

The process of this invention beneficially employs organic and inorganic phosphorus-containing compounds as catalysts. These catalysts include aryl phosphites, preferably represented by the formula $(R^1O)_3P$, and aryl phosphates, preferably represented by the formula $(R^1O)_3PO$ wherein each $R^1$ is independently selected from $C_{6-15}$ aryl moieties, such as phenyl and alkyl-substituted phenyl. Non-limiting examples of aryl phosphites and aryl phosphates include triphenyl phosphite, triphenyl phosphate, tri(methylphenyl)phosphite, tri(methylphenyl)phosphate, and tri(di-t-butylphenyl)phosphite. Other suitable catalysts include aliphatic phosphates, preferably, represented by the formula $(R^2O)_3PO$ wherein each $R^2$ is independently selected from $C_{1-15}$ aliphatic moieties, such as methyl, ethyl, propyl, and higher homologues of these. Non-limiting examples of aliphatic phosphates include trimethyl phosphate, triethyl phosphate, and triisopropyl phosphate. Preferably, the catalyst is an aryl phosphite or aryl phosphate, and more preferably, one in which the aryl moiety is identical to the aryl moiety of the reactive phenol. Accordingly, preferred among the aforementioned catalysts are triphenyl phosphite, triphenyl phosphate, tricresyl phosphite, and tricresyl phosphate. More preferred are triphenyl phosphite and tricresyl phosphite. The most preferred catalyst is triphenyl phosphite.

Other suitable catalysts include organic phosphinites and phosphinates, and organic pyrophosphates represented by Formulas I, II, and III, respectively:

$$R^3P(OR^3)_2 \qquad \text{I}$$

$$R^3P(O)(OR^3)_2 \qquad \text{II}$$

$$(R^3O)_2\text{—}P(O)\text{—}O\text{—}P(O)\text{—}(OR^3)_2 \qquad \text{III}$$

wherein each $R^3$ is independently a $C_{6-15}$ aryl moiety, such as phenyl or alkyl-substituted phenyl, or a $C_{1-15}$ aliphatic moiety, such as methyl, ethyl, or propyl. Preferred organic phosphinites, phosphinates and pyrophosphates include, respectively, trimethyl phosphinite, trimethyl phosphinate, and tetramethyl pyrophosphate.

Other suitable catalysts include inorganic phosphorous and phosphoric acids, such as, phosphoric acid ($H_3PO_4$), phosphorous acid ($H_3PO_3$), and hypophosphorous acid ($H_3PO_2$); as well as, phosphorus oxides which are capable of reacting with phenols to give phosphates, including phosphorus pentoxide ($P_2O_5$) and phosphorus trioxide ($P_2O_3$). Preferred among these catalysts is phosphoric acid.

The aforementioned phosphorus-containing catalysts are generally homogeneous in that they dissolve in the reaction mixture. If desired, any of the phosphorus-containing catalysts can be made heterogeneous by supporting the catalyst on an inorganic support, such as silica, alumina, or a zeolite. Methods of supporting catalysts are well known to those skilled in the art. For example, the catalyst can be applied as a neat liquid or dissolved in a solvent and applied to the support by the well known method of impregnation. Alternatively, the catalyst may be covalently bonded to an organic support, such as a cross-linked polystyrene. For example, the phosphorus-containing catalyst may be reacted with chloromethylated polystyrene beads to yield the corresponding covalently bonded form of the catalyst.

It is noted that the catalysts employed in the process of this invention are sufficiently reactive without the addition of promoters, such as, Group VIII and Group IB metal compounds, including platinum and copper compounds, as well as Lewis acids, such as boron trifluoride.

Any amount of phosphorus-containing catalyst can be employed in the process of this invention. Generally, the molar ratio of phenol to phosphorus-containing catalyst ranges from about 10/1 to about 1000/1, preferably, from about 50/1 to about 500/1, and more preferably, from about 80/1 to about 200/1.

The process of this invention can be conducted in any suitable reactor, including batch reactors, continuous stirred tank reactors (CSTR), bubble columns, trickle beds, and other gas-liquid contact reactors. If the catalyst has been made heterogeneous, then continuous fixed bed, trickle bed, and transport reactors are especially suitable. In preferred designs a CSTR, or a trickle bed, or bubble column is employed. In a more preferred design, a bubble column, optionally, connected to a CSTR is employed.

The process according to this invention is usually carried out in the homogeneous liquid phase. Under these conditions, the phenol or substituted phenol is employed neat in a liquid melt, or alternatively, dissolved in an appropriate solvent. Typically, the gaseous carbonyl halide is contacted with the liquid phase containing the phenol, and the liquid phase is contacted with the catalyst. Preferably, the reaction is conducted in the melt without a solvent. Advantageously, the space-time yield achieved in this manner is higher than that obtained when the reaction is carried out in the presence of solvent. Under some circumstances, it can be beneficial to carry out the reaction in a solvent, especially when the melting point of the phenol is above the desired reaction temperature. Under those conditions the phenol, at least at the start of the reaction, might react slowly if solvent were not present. The presence of solvent can also be advantageous for controlling and removing the heat of the reaction which is exothermic.

The solvent can be any compound which does not react with the carbonyl halide, the phenol, or the phosphorus-containing catalyst. In addition, the solvent should be liquid under the reaction conditions and should be a compound in which the phenol is soluble. Suitable solvents include aliphatic and aromatic hydrocarbons, such as pentane, hexane, cyclohexane, toluene, and xylenes, as well as, chlorinated aromatic and aliphatic hydrocarbons, such as chlorobenzene, dichlorobenzene, trichlorobenzene, chloronaphthalene, and trichloroethane.

Any operable process conditions can be employed provided that an aryl haloformate or diaryl carbonate product is produced. Typically, the process temperature falls between about 50° C. and about 250° C., preferably between about 100° C. and about 190° C. Below the lower typical temperature the conversion of the phenol may be low. Above the typical upper temperature the phenol may boil and condense on the upper walls of the reactor. For the formation of aryl haloformates, the most preferred temperature ranges from about 120° C. to about 160° C. For the formation of diaryl carbonates, even more preferred temperatures range from about 150° C. to about 190° C., and most preferably, from about 170° C. to about 180° C. The process pressure typically ranges between about 0.1 atm and about 10 atm, preferably, between about 0.5 atm and about 2.0 atm, and most preferably, between about 0.8 atm and about 1.0 atm.

When phenol or a substituted phenol and carbonyl halide are contacted in accordance with the process of this invention as disclosed hereinabove, an aryl haloformate or a diaryl carbonate is predominantly produced as the product. Preferably, the aryl haloformate (IV) and diaryl carbonate (V) are represented by the formulas:

$$R^4O-C(O)-X \qquad (IV)$$

and $$R^4O-C(O)-OR^4 \qquad (V)$$

wherein X is chloro, bromo, or fluoro; preferably, chloro; and $R^4$ is a $C_{6-10}$ aryl moiety, which may be further substituted with one or more of the following moieties: $C_{1-10}$ aliphatic, halo, phenyl, $C_{1-10}$ alkyl-substituted phenyl, and ether, ester, and keto moieties, as noted hereinbefore in connection with the aforementioned phenol reactants. More preferably, $R^4$ is phenyl or tolyl, and the more preferred chloroformate is phenyl chloroformate or cresyl chloroformate, while the more preferred diaryl carbonate is diphenyl carbonate or dicresyl carbonate. Most preferably, $R^4$ is phenyl, and the most preferred products are phenyl chloroformate and diphenyl carbonate.

Another preferred product is the bischloroformate represented by the formula:

$$Cl-C(O)-O-R^4-O-C(O)-Cl$$

wherein $R^4$ is defined as above and is preferably phenyl or $C_{1-10}$ alkyl-substituted phenyl. The preferred bischloroformate is the bischloroformate of resorcinol.

Separation of the products from the reactants is carried out by methods well known to those skilled in the art. Unreacted carbonyl halide is flushed from the reactor and connecting lines by means of an inert gas flow, such as a flow of nitrogen or helium. Any unreacted phenol can be recovered by distillation and thereafter recycled to the phosgenation reactor. Diaryl carbonate and aryl haloformate are also recovered by distillation. By-product hydrogen halide leaves the reactor as a gas and can be utilized in other commercial processes. For example, hydrogen chloride can be recycled into the production of phosgene via oxychlorination of carbon monoxide.

For the purposes of this invention, conversion is defined as the mole percentage of carbonyl halide, preferably phosgene, which reacts to form products. Generally, the phosgene conversion is greater than about 80 mole percent, preferably, greater than about 85 mole percent, and more preferably, equal to or greater than about 90 mole percent.

By one method, selectivity can be defined as the mole percentage of converted carbonyl halide which forms diaryl carbonate or aryl haloformate product. Alternatively, selectivity can be defined as the mole percentage of converted phenol which forms diaryl carbonate or aryl haloformate product. By either definition the process of this invention is capable of achieving selectivities to diaryl carbonate or aryl haloformate greater than about 85 mole percent, preferably, greater than about 90 mole percent, and more preferably, greater than about 95 mole percent.

The following examples are illustrative of the claimed invention, but are not intended to be limiting thereof.

EXAMPLE 1

Preparation of Phenyl Chloroformate Using Triphenylphosphite

A four-necked flask equipped with a gas inlet, a dry ice condenser, a mechanical stirrer, a thermocouple and a sampling port is charged with phenol (Aldrich, 287.5 g, 2.907 mol) and triphenyl phosphite (10.12 g, 32.61 mmol). The temperature is raised to 140° C. and phosgene (274 g, 2.77 mol) is added over a 465 minute period. Phosgene/phenol molar ratio is 0.95. A recirculating aqueous sodium hydroxide scrubber is used to neutralize the coproduct hydrochloric acid and to destroy traces of phosgene which are not condensed in the condenser. After the phosgene addition is stopped, a nitrogen stream is used to purge residual phosgene and the reactor is cooled to ambient temperature. The colorless crude product is isolated by vacuum distillation to give phenyl chloroformate (417.84 g, bp 73°–77° C. at 14 mm Hg) containing 6.6 percent by weight residual phenol. Selectivity to phenyl chloroformate is 95 mole percent based on phenol, 90 mole percent based on phosgene.

EXAMPLE 2

Preparation of Diphenyl Carbonate Using Triphenyl Phosphite

The reactor described in Example 1 is charged with phenol (273.0 g, 2.760 mol) and triphenylphosphite (9.107 g, 29.35 mmol). Phosgene (121.2 g, 1.23 mol) is passed into the reactor for 267 min. Phosgene/phenol molar ratio is 0.45. The reactor temperature is raised to 170° C. for 20 hr during which a slow nitrogen stream is used to purge phosgene and gaseous hydrochloric acid. The crude contents are distilled to give a fraction containing unreacted phenol (69.28 g, bp 75°–80° C. at 14 mm Hg) and a high boiling fraction containing diphenyl carbonate (225.36 g, bp 170°–174° C. at 15 mm Hg). Selectivity to diphenyl carbonate is 97 mole percent based on phenol, 86 mole percent based on phosgene.

EXAMPLE 3

Preparation of Diphenyl Carbonate Using Phosphoric Acid

The reactor of Example 1 is charged with phenol (273.0 g, 2,760 mol), diphenylmethane (1.5646 g), and 85 weight percent phosphoric acid (9.635 g, 83.6 mmol). The diphenylmethane is employed as an internal standard for the gas chromatographic (GC) analysis. Phosgene (84.6 g, 0.86 mol) is passed into the reactor for 143 min. Phosgene/phenol molar ratio is 0.31. An aliquot (50 μL) is removed via syringe and analyzed by GC to yield diphenyl carbonate (44.7 mmol), phenyl chloroformate (341 mmol), phenol (2.26 mol) and triphenylphosphate (12.0 mmol). The reactor temperature is raised to 170° C. for 18 hr during which time a slow nitrogen stream is used to purge phosgene and gaseous hydrochloric acid. The crude contents are distilled to give a fraction containing unreacted phenol (184.21 g) and a high boiling fraction containing diphenyl carbonate (42.65 g). The pot residue contains residual diphenyl carbonate (29.2 g) and triphenylphosphate (25.61 g). Selectivity to diphenyl carbonate is 42 mole percent based on phenol, 39 mole percent based on phosgene. Part of the phenol is consumed in a reaction with phosphoric acid to yield triphenyl phosphate.

EXAMPLE 4

Preparation of Phenyl Chloroformate Using Hypophosphorous Acid

The reactor of Example 1 is charged with phenol (319.0 g, 3.390 mol), diphenylmethane as an internal GC standard (3.0723 g), and 50 weight percent hypophosphorous acid (7.046 g). Phosgene (64.6 g, 0.65 mol) is passed into the reactor for 90 min. Phosgene/phenol molar ratio is 0.19. After heating at 120° C. an additional 4 hr the reactor is cooled to ambient temperature. Analysis by GC yields diphenyl carbonate (29.1 mmol), phenylchloroformate (156.7 mmol) and phenol (2.96 mol). Selectivity to phenylchloroformate is 36 mole percent based on phenol, 24 mole percent based on phosgene. Part of the phenol is consumed in a reaction with hypophosphorous acid to yield triphenyl phosphate.

What is claimed is:

1. A process of preparing diaryl carbonates or aryl haloformates comprising contacting phenol or a substituted phenol with a carbonyl halide, the molar ratio of carbonyl halide to the phenol being in a range sufficient to prepare predominantly a diaryl carbonate or an aryl haloformate, the contacting of the phenol with carbonyl halide being conducted in the presence of a catalytic amount of a catalyst selected from the group consisting of alkyl phosphates, aryl phosphates, organic phosphinates, organic pyrophosphates, inorganic phosphorous and phosphoric acids, phosphorus oxides, and mixtures thereof, and the contacting being conducted under reaction conditions such that an aryl haloformate or a diaryl carbonate is formed.

2. The process of claim 1 wherein the substituted phenol contains one or more substituents selected from the group consisting of $C_{1-10}$ aliphatic, halo, phenyl, $C_{1-10}$ alkyl-substituted phenyl, ether, keto, and ester moieties.

3. The process of claim 1 wherein phenol is employed.

4. The process of claim 1 wherein the carbonyl halide/phenol molar ratio ranges between about 0.6 and 1.2, and the predominant product is an aryl haloformate.

5. The process of claim 1 wherein the carbonyl halide/phenol molar ratio ranges between about 0.1 and 0.5, and the predominant product is a diaryl carbonate.

6. The process of claim 1 wherein the aryl phosphates are represented by the formula $(R^1O)_3PO$ wherein each $R^1$ is independently selected from $C_{6-15}$ aryl or alkyl-substituted aryl moieties.

7. The process of claim 6 wherein the aryl phosphate is triphenyl phosphate or tricresyl phosphate.

8. The process of claim 1 wherein the aliphatic phosphate is represented by the formula $(R^2O)_3PO$ wherein each $R^2$ is independently selected from the group consisting of $C_{1-15}$ aliphatic moieties.

9. The process of claim 1 wherein the organic phosphinates, and organic pyrophosphates are represented by Formulas II, and III, respectively:

$$R^3P(O)(OR^3)_2 \qquad \text{II}$$

$$(R^3O)_2-P(O)-O-P(O)-(OR^3)_2 \quad \text{III}$$

wherein each $R^3$ is independently a $C_{6-15}$ aryl moiety or a $C_{1-15}$ aliphatic moiety.

10. The process of claim 1 wherein the organic phosphinate is trimethyl phosphinate, and the organic pyrophosphate is tetramethyl pyrophosphate.

11. The process of claim 1 wherein the inorganic phosphorous acid is phosphorous acid or hypophosphorous acid; wherein the phosphoric acid is phosphoric acid; and wherein the phosphorus oxide is phosphorus pentoxide or phosphorus trioxide.

12. The process of claim 1 wherein the phenol/catalyst molar ratio ranges from about 10/1 to about 1000/1.

13. The process of claim 1 wherein the temperature ranges from about 50° C. to about 250° C. and wherein the pressure ranges from about 0.1 atm to about 10 atm.

14. The process of claim 1 wherein the process is conducted in a reactor selected from continuous stirred tank reactors, trickle bed reactors, and bubble column reactors.

15. The process of claim 1 wherein the aryl haloformate is represented by the formula:

$$R^4O-C(O)-X$$

wherein X is chloro, bromo, or fluoro, and $R^4$ is a $C_{6-10}$ aryl moiety, optionally substituted with one or more $C_{1-10}$ aliphatic, halo, phenyl, $C_{1-10}$ alkyl-substituted phenyl, ether, ester, or keto moieties; or wherein the aryl haloformate is represented by the formula:

$$Cl-C(O)-O-R^4-O-C(O)-Cl$$

wherein $R^4$ is as defined hereinabove; and wherein the diaryl carbonate is represented by the formula:

$$R^4O-C(O)-OR^4$$

wherein $R^4$ is as defined hereinabove.

16. The process of claim 15 wherein the aryl haloformate is phenyl chloroformate, cresyl chloroformate, or the bischloroformate of resorcinol, and wherein the diaryl carbonate is diphenyl carbonate or dicresyl carbonate.

17. The process of claim 1 wherein the selectivity to diaryl carbonate or aryl haloformate, based on carbonyl halide or phenol converted, is greater than about 85 mole percent.

18. The process of claim 1 wherein the phosphorus-containing catalyst is applied to or chemically bonded to a support.

19. A process for the preparation of phenyl chloroformate or diphenyl carbonate comprising contacting phenol with phosgene in the presence of a catalytic amount of a phosphorus-containing catalyst selected from the group consisting of aryl phosphates, alkyl phosphates, organic phosphinates, organic pyrophosphates, inorganic phosphoric and phosphorous acids, phosphorus oxides, and combinations thereof, wherein when the contacting occurs at a phosgene/phenol molar ratio between 0.6 and about 1.2, a temperature between about 120° C. and about 160° C., a pressure between about 0.1 atm and 10 atm, the product formed is predominantly phenyl chloroformate, and wherein when the contacting occurs at a phosgene/phenol molar ratio between about 0.1 and about 0.5, a temperature between about 150° C. and about 190° C., and a pressure between about 0.1 atm and 10 atm, the product formed is predominantly diphenyl carbonate.

* * * * *